United States Patent
Knoch et al.

[11] Patent Number: 5,312,046
[45] Date of Patent: May 17, 1994

[54] LIQUID ATOMIZER

[75] Inventors: Martin Knoch, Berg; Andreas Lintl, Starnberg, both of Fed. Rep. of Germany

[73] Assignee: Paul Ritzau Pari Werk GmbH, Fed. Rep. of Germany

[21] Appl. No.: 948,484

[22] Filed: Sep. 22, 1992

[30] Foreign Application Priority Data

Nov. 7, 1991 [EP] European Pat. Off. ........ 91118993.4

[51] Int. Cl.$^5$ ............................................ A61M 11/00
[52] U.S. Cl. .................................... 239/338; 239/370; 128/200.18; 128/200.21
[58] Field of Search .............................. 239/338, 370; 128/200.18, 200.21

[56] References Cited

U.S. PATENT DOCUMENTS

| | | | |
|---|---|---|---|
| 4,560,519 | 12/1985 | Cerny | 239/338 X |
| 4,588,129 | 5/1986 | Shanks | 239/338 |
| 4,657,007 | 4/1987 | Carlin et al. | 128/200.18 |

FOREIGN PATENT DOCUMENTS

| | | | |
|---|---|---|---|
| 483193 | 5/1977 | Australia | 128/200.21 |
| 0171726 | 2/1986 | European Pat. Off. | |
| 439361 | 1/1927 | Fed. Rep. of Germany | 128/200.21 |
| 8437274 | 11/1985 | Fed. Rep. of Germany | |
| 8614551 | 7/1986 | Fed. Rep. of Germany | |
| 8905364 | 8/1989 | Fed. Rep. of Germany | |
| 2023023 | 12/1979 | United Kingdom | |

*Primary Examiner*—Andres Kashnikow
*Assistant Examiner*—Lesley D. Morris
*Attorney, Agent, or Firm*—Wegner, Cantor, Mueller & Player

[57] ABSTRACT

A liquid atomizer having only two housing sections, which can be forced into engagement, so that the prescribed distances within the segment forming the nozzle body are set semi automatically. In addition, at least one of the housing sections is equipped with a springy element, which, however, is designed integrally with the housing section. The springy element may be a weakened wall segment.

18 Claims, 4 Drawing Sheets

LIQUID ATOMIZER

FIELD OF THE INVENTION

The invention relates to a liquid atomizer to generate an aerosol especially for inhalation purposes.

BACKGROUND OF THE INVENTION

Liquid atomizers for inhalation purposes are known in various embodiments. Thus, for example from DE 32 38 149 A1 an atomizer is known, which comprises a bottom and an upper housing section. The bottom housing section forms the container for the liquid to be atomized, and includes a base equipped with the pressure gas supply line. The interior of the housing has, separated from it, a nozzle body in continuation of the pressure gas channel and an air supply chamber opposite thereto formed in the bottom housing section. The nozzle body is removably attached to the upper housing section. Between nozzle body and air supply chamber is a gas current controller, again separated from the remaining components, which extends from the end of the nozzle body that faces the air supply channel. A discharge pipe for the aerosol is molded on the side to the upper housing section. The nozzle body includes two bores through which the liquid is sucked from the liquid collection region of the bottom housing section. The bottom housing section can be separated from the upper housing section or the nozzle body can be separated from the bottom housing section in order to be able to clean the nozzle channels and the entire atomizer.

Another liquid atomizer, which comprises an upper housing section with an air supply channel and a bottom housing section with a pressure gas connection, is know form AU 3,429,389 B. A short discharge pipe for the aerosol generated in the housing interior is molded on the side to the upper housing section and an air supply chamber projecting into the housing interior is molded on in the center of the upper region. A nozzle body, whose bottom end includes the connecting part of a centrally extending pressure gas channel, is removably attached to the pressure gas connection disposed in the center of the bottom housing section. The nozzle body aligns with the air supply chamber, so that the atomizing end of the nozzle body is opposite the air supply chamber. The atomizing end of the nozzle body has a receptacle for another component of the atomizer, which bears a gas current controller. This component is mounted in such a manner along the housing wall on the nozzle body that the gas current controller is disposed above the atomizing end opposite the openings of the pressure gas channel and the liquid channels. Furthermore, the known atomizer has two annular deflecting elements, which are disposed in such a manner in the interior of the housing that a deflection and distribution and a stilling of the generated aerosol is brought about.

The two atomizers described as examples exhibit a drawback shared with other previously known atomizers. Since the atomizers, in particular the nozzle bodies, always have to be carefully cleaned in order to remove completely any residues from the aerosol liquids the known atomizers must be dissectable in such a manner that the nozzle body and in particular the liquid channels can be cleaned. In addition, the prior art atomizers can be disassembled into several, often very small parts. Therefore, the user not only has to quite scrupulously clean the device, but also must be able to disassemble the atomizer into its individual components and assemble it again. In so doing, there is a high risk that one of the small parts of the atomizer will be lost.

Moreover, it is necessary that the design of the nozzle body, in particular the liquid channels, and the position of the gas current controller with respect to the atomizing end of the nozzle body, be constructed within small tolerances. Thus, the components that affect the flow of the liquid/air mixture must be arranged at precise intervals and in precise relationships to each other, in order to generate a finely distributed, well mixed, and homogeneous aerosol. For this reason the nozzle body was manufactured to date separately from the housing of the atomizer and always installed separately from said housing. In most cases the other parts influencing the flow were also manufactured separately from the housing and connected detachably to said housing.

SUMMARY OF THE INVENTION

Starting from this prior art, the invention is based on the problem of providing a liquid atomizer, which comprises a small number of individual parts, and still enables a thorough cleaning of the parts making contact with the aerosol liquid.

This problem is solved for an atomizer with the features of the present invention.

Other advantageous embodiments are contemplated. Preferably the atomizer comprises only two housing sections, which can be forced into engagement, so that the prescribed distances within the segment forming the nozzle body are set semi-automatically. In addition, at least one of the housing sections is equipped with a springy element, which, however, is designed integrally with the housing section. Preferably it is a weakened wall segment.

The two-part construction of the atomizer according to the invention is advantageous for the user and leads to the atomizer being dissectable and cleanable in a very simple manner. This applies in particular to the liquid channels, which in the case of an advantageous embodiment are accessible immediately after disassembling the atomizer.

However, the atomizer can also exhibit an outer nozzle body, which is detachable from the housing section, so that another material or another mode of manufacture can be used for the nozzle body.

BRIEF DESCRIPTION OF THE DRAWINGS

In the following the invention is described in detail with one embodiment with reference to the drawings.

DETAILED DESCRIPTION OF THE PREFERRED EMBODIMENTS

Figure 1:
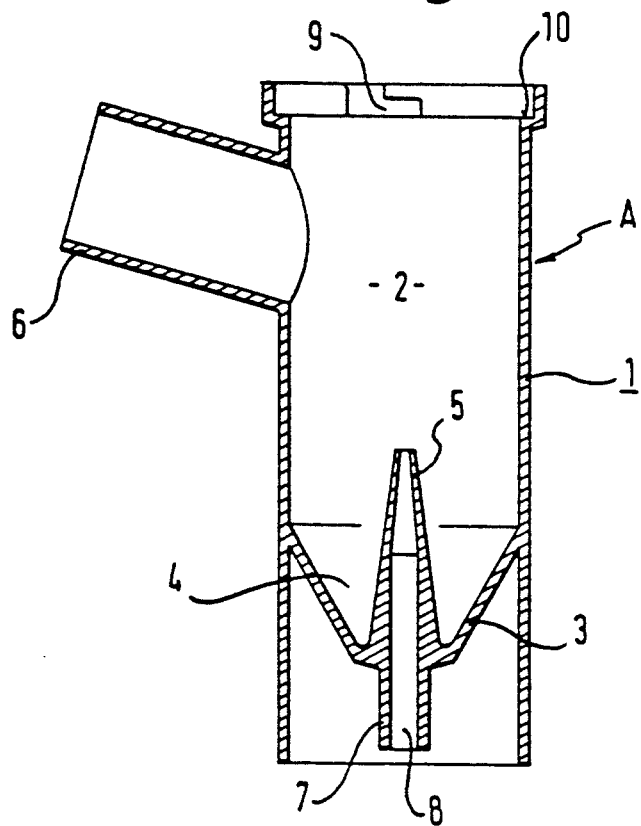
FIG. 1 is a side cross-sectional view of a first housing section of a liquid atomizer according to the invention.
Figure 2:
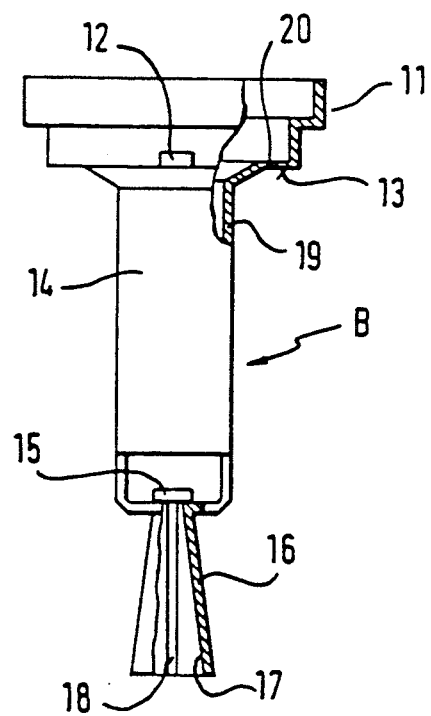
FIG. 2 is a side elevational view, partially in cross-section, of a second housing section of a liquid atomizer according to the invention.
Figure 3:
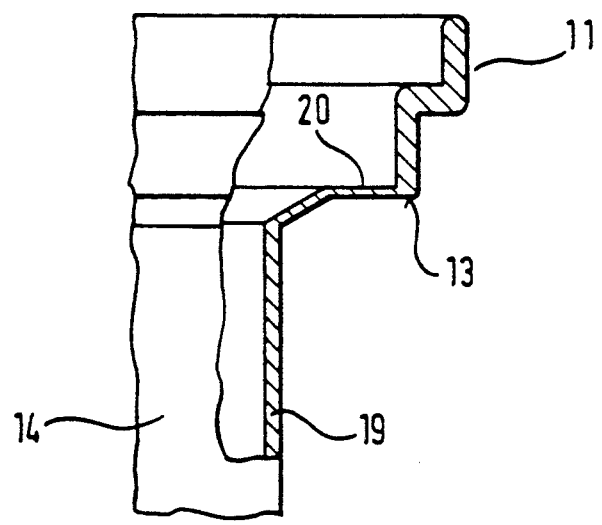
FIG. 3 is an enlarged, partially cross-sectional view of a region of the second housing section of FIG. 2.
Figure 4:
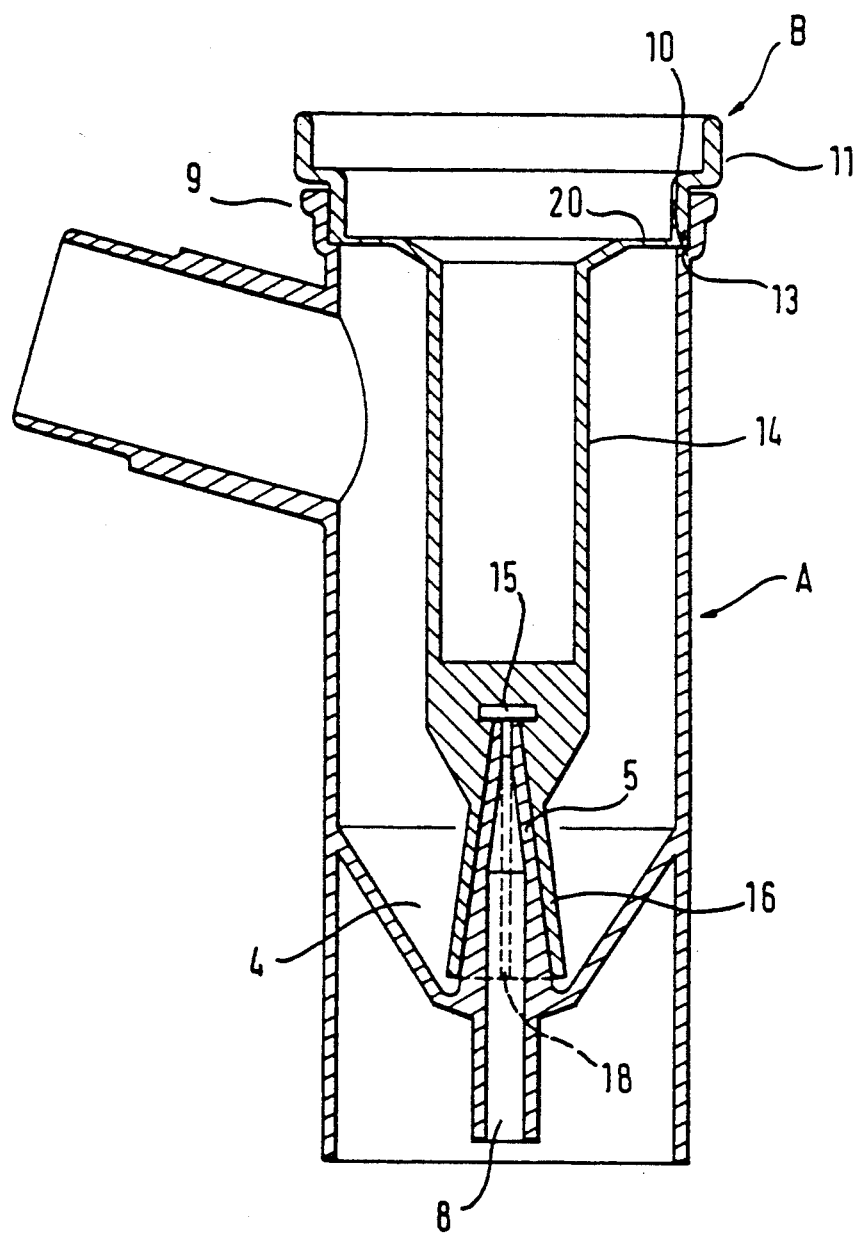
FIG. 4 is a cross-sectional view of the liquid atomizer of the invention that comprises the two housing sections of FIG. 1 and 2.
Figure 5:
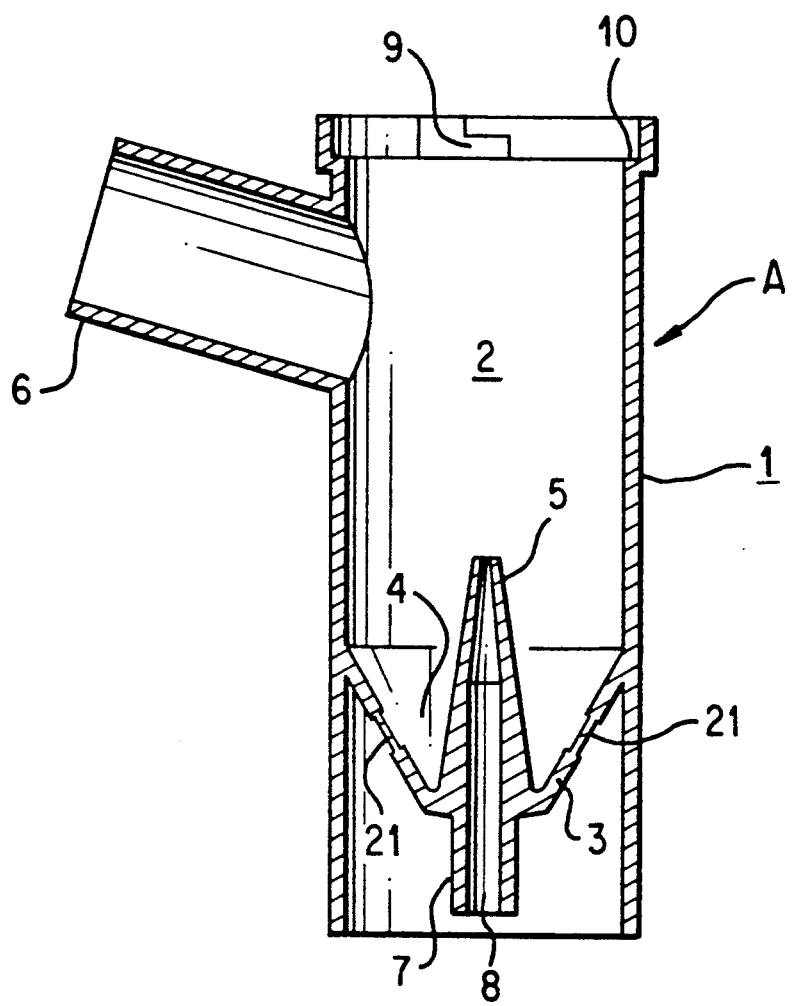
FIG. 5 is a side cross-sectional view of the first housing section according to another preferred embodiment of the invention.

FIG. 1 shows a first housing section A of an embodiment of the liquid atomizer according to the invention.

The cylindrical base body 1 envelops a nebulizing chamber 2, which is closed at the bottom with a wall 3 of a liquid collection region 4 and an inner part 5 of the atomizing nozzle. A short aerosol discharge pipe 6 is attached on the side to the first housing section A. The cylindrical base body 1, the wall 3 of the liquid collection chamber, the inner part 5 of the atomizing nozzle and the short aerosol connecting pipe 6 are formed as one piece.

The inner part 5 of the atomizing nozzle is preferably conically-shaped and includes a connection 7 for the pressure gas line on the end lying outside the nebulizing chamber 2 through which the pressurized gas, usually air, is fed to a pressure gas channel 8 in the inner part 5 of the atomizing nozzle. The supplied pressure gas issues from the end of the inner part 5 that projects into the nebulizing chamber 2.

The first housing section includes a first connector 9 disposed on the end opposite the liquid collection region 4, preferably in the form of grooves of a bayonet catch. A suitable thread or a snap lock can also be provided as a connector. Furthermore, the first housing section A has a first stop face 10, which interacts with the second housing section described in the following.

FIG. 2 shows the second housing section B of the embodiment of the atomizer according to the invention. The second housing section B is also essentially rotationally symmetrical. On the upper end of the second housing section B is a second connector 11, which corresponds to the connector 9 of the first housing section A. FIG. 2 shows as an example a bracket 12, which can be caught and locked in the grooves of the bayonet catch shown in FIG. 1. A second stop face 13 of the second housing section B is provided to engage with the stop face 10 of the first housing section A.

An air supply chamber 14, which is open both on its upper end in the region of the second connector 11 and also on its opposing bottom end, is formed as one piece with the second connector 11. Furthermore, a gas current controller, which extends diagonally to the substantially circular opening of the air supply chamber 14, is formed on the bottom end of the air supply chamber 14. An outer part 16 of the atomizing nozzle is disposed below the gas current controller 15, which, as will be described in greater detail below in connection with FIG. 4, is joined to the inner part 5 of the atomizing nozzle. The inner wall 17 of the outer part 16 of the atomizing nozzle is configured in accordance with the shape of the inner part 5 of the atomizing nozzle. Furthermore, the inner wall includes at least one, preferably, however, two diametrically opposite grooves 18, which form the liquid channels. If two grooves 18 are provided, they are to be arranged in such a manner on both sides of the gas current controller 15 that a connecting straight line extends between them vertically to the plane of the gas current controller 15.

FIG. 3 shows the upper region of the second housing section B on an enlarged scale. This drawing shows clearly the connector of the second housing section B and the stop face 13. Furthermore, the wall 19 of the air supply chamber 14 is shown as partially cut away. It is also evident that the wall segment 20, which connects the second connector 11 to the air supply chamber 14, is thinner than the wall 19 of the air supply chamber or the second connector 11. Owing to this design, the air supply chamber 14, and with it the outer part 16 of the atomizing nozzle, can be shifted relative to the second connector 11 of the second housing section B, as is described in greater detail in the following with reference to FIG. 4, because the wall region 20 acts as a springy or flexible element, which produces the connector between the air supply chamber 14 and the second connector 11. As an alternative, a bellow can also be provided that allows a displacement between air supply chamber 14 and the second connector 11 of the second housing section B.

FIG. 4 shows the atomizer according to the invention in the assembled state. The outer part 16 of the atomizing nozzle sits on the inner part 5 of the atomizing nozzle, since the outer or inner surface of the two parts are configured to match each other. The outer wall of the inner part 5 forms together with the grooves 18, which are provided in the inner wall 17 of the outer part 16, liquid channels, which connect the liquid collection region to the upper end of the atomizing nozzle. A suitable choice of material and the conical configuration of the two engaging surfaces of the inner or outer part of the atomizing nozzle provide for an exact alignment of the liquid channels 18 and the pressure ga channel 8, in particular in the upper region, i.e. with respect to the gas current controller 15. The linear tolerances, which are to be maintained especially in this region, are maintained on account of the automatic alignment of the engaging parts 5 and 16. A suitable embodiment of the conical inner part 5 and of the outer part 16 of the atomizing nozzle causes no special manufacturing problems, so that even mass production is possible while maintaining the narrow tolerances with respect to the parts effecting the flow of the liquid/air mixture, since the components exerting an influence here are arranged close together and can be well aligned.

The stop face 10 of the first housing section A rests against the stop face 13 of the second housing section B in the region of the connector 9 and 11 of the first or second housing section. The first housing section A is removably attached with the aid of the provided connectors to the second housing section B. Even though the tolerance requirements are not very high in this region of the atomizer, the connectors can also be designed with narrow tolerances, so that a tight fitting lock and a good seal of the nebulizing chamber is guaranteed. This is because the wall region 20 enables a compensating displacement in the axial direction, so that it is not necessary to maintain tight tolerances between the region of the two connectors 9 or 11 and the region of the atomizing nozzle. The sole prerequisite is that the air supply chamber 14 be adequately long in order to guarantee that the outer part 16 of the atomizing nozzle fits snugly on the inner part 5, whereby simultaneously the stop face 10 must engage with the stop face 13. The wall 20 is then bent slightly upwardly in the assembled state of the atomizer and exerts a force acting in the direction of a firm seat on the assembled atomizing nozzle, thus resulting in an exact alignment and maintenance of the specified tolerances in this important region.

In the above described embodiment the wall region 20 acts as a springy element and allows the air supply chamber to be moved in the longitudinal direction of the atomizer. In a similar manner, however, a springy element can also be provided in the form of a bellow in the upper region of the air supply chamber 14. The first housing section also offers possibilities of providing a springy region 21, for example in the region of the wall 3 of the liquid collection chamber 4, as shown in FIG. 5. However, springy elements can also be provided on both housing sections. The decisive factor is that an axial displacement of the region of the atomizing nozzle relative to the region of the connectors is possible. Because in this manner an exact alignment of the parts forming the nozzle body is possible without having to observe tolerances over a long distance, namely between the two aforementioned regions. The wall region acting as the springy element should be adequately rigid with respect to twisting, in order to avoid a twisted positioning of the liquid channels 18 with respect to the short discharge pipe 6. However, embodiments which demand that this aspect be observed are possible.

We claim:

1. A two-piece liquid atomizer, comprising:
   a first piece formed of a first housing section, which includes
      an inner part of an atomizing nozzle, and
      a first connector;
   a second piece formed of a second housing section, which includes;
      an outer part of the atomizing nozzle adapted to engage the inner part in order to form the atomizing nozzle, and
      a second connector, adapted to engage the first connector for the connection of the second housing section with the first housing section to form a nebulizer chamber; and
   springy means integrally formed with either the first housing section or the second housing section for allowing compensating movement between the inner and outer parts of the atomizing nozzle and the first and second connectors when the first and second housing sections are in their assembled state.

2. A liquid atomizer as claimed in claim 1, wherein the springy means is a springy wall region of the first and second housing section.

3. A liquid atomizer as claimed in claim 1, wherein the inner part is formed as one piece with the first housing section.

4. A liquid atomizer as claimed in claim 1, wherein the inner part is conically-shaped with an outer wall configured to engage the outer part.

5. A liquid atomizer as claimed in claim 1, wherein an interior of the inner part includes a pressure air channel.

6. A liquid atomizer as claimed in claim 1, wherein the inner part is formed as one piece with a wall of a liquid collection region in the first housing section.

7. A liquid atomizer as claimed in claim 1, wherein the inner part is formed as a continuation of a pressure gas connection.

8. A liquid atomizer as claimed in claim 1, wherein the first connector includes a stop face.

9. A liquid atomizer as claimed in claim 1, wherein the first connector includes grooves of a bayonet catch.

10. A liquid atomizer as claimed in claim 1, wherein the outer part is formed as one piece with the second housing section.

11. A liquid atomizer as claimed in claim 1, wherein the outer part is internally conically-shaped with an inner wall.

12. A liquid atomizer as claimed in claim 11, wherein the inner wall of the outer part includes at least one groove to form at least one liquid channel.

13. A liquid atomizer as claimed in claim 1, wherein the second housing section includes a gas current controller disposed opposite the outlet end of the atomizing nozzle.

14. A liquid atomizer as claimed in claim 1, wherein the second housing section encloses an air supply chamber, on whose one end the second connector is arranged and on whose other end the outer part of the atomizing nozzle is arranged.

15. A liquid atomizer as claimed in claim 1, wherein the second housing section includes a stop face.

16. A liquid atomizer as claimed in claim 1, wherein the second connector includes a bracket of a bayonet lock.

17. A liquid atomizer as claimed in claim 1, wherein the first and second connectors are connected by a snap connection.

18. A liquid atomizer as claimed in claim 1, wherein a short aerosol discharge pipe is molded to the first housing section.

* * * * *